United States Patent
Benson et al.

(10) Patent No.: US 7,306,951 B1
(45) Date of Patent: Dec. 11, 2007

(54) METHOD AND APPARATUS FOR DETERMINING DIFFUSIBLE HYDROGEN CONCENTRATIONS

(75) Inventors: David K. Benson, Golden, CO (US); Thomas R. Wildeman, Golden, CO (US); R. Davis Smith, Wheat Ridge, CO (US); David L. Olson, Golden, CO (US)

(73) Assignee: Midwest Research Institute, Kansas City, MO (US)

( * ) Notice: Subject to any disclaimer, the term of this patent is extended or adjusted under 35 U.S.C. 154(b) by 496 days.

(21) Appl. No.: 09/937,208

(22) PCT Filed: Jun. 8, 2000

(86) PCT No.: PCT/US00/15752

§ 371 (c)(1),
(2), (4) Date: May 28, 2002

(87) PCT Pub. No.: WO00/75634

PCT Pub. Date: Dec. 14, 2000

Related U.S. Application Data

(60) Provisional application No. 60/138,144, filed on Jun. 8, 1999.

(51) Int. Cl.
| | |
|---|---|
| *G01D 18/00* | (2006.01) |
| *G01N 3/62* | (2006.01) |
| *G01N 21/00* | (2006.01) |
| *G01N 27/00* | (2006.01) |
| *G01N 31/00* | (2006.01) |
| *G01N 33/00* | (2006.01) |
| *G01N 35/00* | (2006.01) |
| *G01N 37/00* | (2006.01) |
| *G01N 7/00* | (2006.01) |
| *G01N 9/00* | (2006.01) |
| *G01N 33/497* | (2006.01) |
| *G01N 33/20* | (2006.01) |
| *G01R 35/00* | (2006.01) |
| *G01S 7/40* | (2006.01) |
| *G01W 1/18* | (2006.01) |
| *G12B 13/00* | (2006.01) |
| *B32B 5/02* | (2006.01) |

(52) U.S. Cl. .................. 436/144; 73/19.07; 73/1.02; 73/1.06; 73/1.16; 73/19.01; 73/23.2; 73/31.05; 73/1.01; 436/164; 422/83; 422/88

(58) Field of Classification Search ............... 436/144; 73/1.01, 1.02, 1.06, 1.16, 19.01, 19.07, 23.2, 73/31.05

See application file for complete search history.

(56) References Cited

U.S. PATENT DOCUMENTS

| | | | |
|---|---|---|---|
| 4,050,895 A | 9/1977 | Hardy et al. | |
| 4,142,399 A | 3/1979 | Sato et al. | |
| 4,192,175 A * | 3/1980 | Godai et al. ................ 73/19.02 |
| 4,221,651 A * | 9/1980 | Mansfeld et al. ........... 204/412 |
| 4,475,963 A * | 10/1984 | Takahashi et al. .......... 148/503 |
| 4,600,310 A * | 7/1986 | Cramp et al. ................ 356/432 |
| 4,734,577 A * | 3/1988 | Szuchy .................... 250/227.16 |
| 5,107,316 A * | 4/1992 | Jelley et al. ................. 257/432 |
| 5,153,931 A * | 10/1992 | Buchanan et al. ............ 385/12 |
| 5,279,169 A * | 1/1994 | Freeman ..................... 73/866 |
| 5,405,583 A | 4/1995 | Goswami et al. | |
| 5,436,167 A | 7/1995 | Robillard | |
| 5,445,725 A * | 8/1995 | Koide et al. ................. 205/790 |
| 5,632,958 A | 5/1997 | Kane et al. | |
| 5,708,735 A * | 1/1998 | Benson et al. ................ 385/12 |
| 5,728,422 A | 3/1998 | Kane et al. | |
| 5,783,152 A | 7/1998 | Nave | |
| 5,939,020 A | 8/1999 | Glaunsinger et al. | |
| 6,096,560 A | 8/2000 | Scripca et al. | |
| 6,120,936 A * | 9/2000 | Young et al. ............. 429/218.2 |
| 6,185,344 B1 * | 2/2001 | Bevenot et al. ............... 385/12 |
| 6,277,589 B1 * | 8/2001 | Seibert et al. ................ 435/30 |
| 6,328,932 B1 * | 12/2001 | Carter et al. ............. 422/82.06 |

OTHER PUBLICATIONS

Skoog, D.A., and Leary, J., Principles of Instrumental Analysis, Saunders College Publishing Co., Fourth Edition, 1992, p. A-17.

Crank, J., The Mathematics of Diffusion, Oxford Science Publishing Co., 1992, p. 32.
Volkl, J., and Alefeld, G., "Diffusion of Hydrogen in Metals," Hydrogen in Metals I, Volkl, J., and Alefeld, G., ed., Springer-Verlag, New York, 1978, pp. 321-348.

* cited by examiner

*Primary Examiner*—Jill Warden
*Assistant Examiner*—Keri A Moss
(74) *Attorney, Agent, or Firm*—Paul J. White

(57) ABSTRACT

A measuring apparatus and method for use in measuring diffusible hydrogen concentrations in materials, structures, and other objects. In an embodiment of the invention for use in welding applications, the measuring apparatus (10) includes a sensor assembly (20) that, with an included sealing member (40), defines a sample area (17) on a weld bead (16) from which hydrogen evolves into a sample volume (18) defined by the sealing member (40), a sensor housing (34) and a sensor (22) of the sensor assembly (20). The hydrogen reacts with a sensing layer (28) and a reflector layer (30) positioned on the end of an optical fiber (24), all of which are included in the sensor assembly (20) and are sealably positioned within the sensor (22). The sensing layer (28) comprises a chemochromic material that undergoes changes in physical properties, such as optical transmission properties, when it reacts with hydrogen and these changes are measured by the measuring apparatus (10) to determine the amount of hydrogen evolving from the sample area (17). An optical fiber (46) is joined to the sensor optical fiber (24) to direct light (63) transmitted by a light source (62) in a hydrogen monitoring assembly (60) through the sensing layer (28) to strike the reflector layer (30) which reflects light (67) back through optical fiber (46) to a detector (68) in the hydrogen monitoring assembly (60). A signal analyzer (72) is included in the hydrogen monitoring assembly (60) and is calibrated and configured to measure the diffusible hydrogen concentration in the weld bead (16) based on measured changes in the optical transmission properties of the sensing layer (28).

45 Claims, 3 Drawing Sheets

METHOD AND APPARATUS FOR DETERMINING DIFFUSIBLE HYDROGEN CONCENTRATIONS

CROSS-REFERENCE TO RELATED PATENT APPLICATIONS

This application claims the benefit of U.S. Provisional Application Ser. No. 60/138,144, filed Jun. 8, 1999.

TECHNICAL FIELD

The present invention relates generally to a method and apparatus for determining diffusible hydrogen concentrations in a material sample, and more particularly, to a method and apparatus that converts measured changes in the physical properties, such as optical absorption, of a sensor element into an output signal that is closely correlated to the diffusible hydrogen content of the sample.

BACKGROUND ART

High concentrations of hydrogen dissolved in construction and fabrication materials are an ongoing concern because hydrogen concentrations can alter the mechanical properties of the materials causing cracking, embrittlement, weakening, and other detrimental changes. Hydrogen may be introduced into materials by a number of processes including, for example, arc welding, extended exposure to pressurized gases containing hydrogen, various corrosion processes, and repeated exposure to high pressure gases containing hydrogen, such as in cannon barrels. Hydrogen damage is of particular concern with the use of metals, and, in particular, steels which are susceptible to hydrogen embrittlement, hydrogen induced cracking (HIC), hydrogen assisted cracking (HAC), and other hydrogen-induced damage. Generally, there is an acceptable concentration of introduced or dissolved hydrogen for each material above which the material is considered unsafe or unsatisfactorily weak for its intended use.

The buildup of hydrogen in steel is of particular concern in fabrication and construction processes relying heavily on arc welding. During arc welding, atomic hydrogen is produced in the arc by the decomposition of hydrogenous compounds, such as water, lubricants, or molecular hydrogen in the air or base metal, which enter the arc. The atomic hydrogen is soluble in the liquid weld pool or bead and is retained within the weld material as it freezes or solidifies. However, a portion of the hydrogen, i.e., diffusible fraction, rapidly diffuses out of the metal even at normal room temperatures. The diffusible fraction is generally accepted as a primary indicator of potential hydrogen damage of the welded joint, with initial hydrogen concentrations being particularly useful in predicting damage. Therefore, measurement of diffusible hydrogen concentrations can provide an effective determination of whether a welded joint has a hydrogen concentration that is below an acceptable concentration limit, e.g., determining, at least in part, the quality or strength of the welded joint.

Current industry practice for assuring the quality of welds involves the development of a standard welding procedure, which is then followed during all welding processes. Under ANSI/AWS A4.3-93 "Standard Methods for Determination of the Diffusible Hydrogen Content of Martensitic, Bainitic, and Ferritic Steel Weld Metal Produced by Arc Welding" by the American Welding Society, a welding procedure is qualified by welding four (4) samples or coupons of a particular steel, promptly quenching the steel coupons to low temperatures, and then testing the steel coupons for diffusible hydrogen concentration. The diffusible hydrogen concentration is measured in units of volume of gas per weight of deposited metal, e.g., milliliters of hydrogen per 100 grams of deposited weld metal. The volume of hydrogen is measured under current standard procedures either by volumetric displacement of mercury by placing the sample in a audiometer and allowing hydrogen to diffuse from the sample for at least 72 hours or by baking each sample in a sealed container for an extended period to evolve gases and then analyzing the gases in a gas chromatograph to identify the volume of hydrogen.

While such methods of measuring the volume of diffusible hydrogen in samples provide relatively accurate measurements of the diffusible hydrogen content in each sample, they do have a number of significant limitations and problems. First, these methods measure bulk or total diffusible hydrogen evolving from the sample and do not provide a method of identifying concentrations of hydrogen or, more particularly, localized concentrations of hydrogen. Such, localized concentrations of hydrogen, when combined with residual stresses at inclusions, grain boundaries, or the weld fusion lines, can cause cracks to occur even though overall diffusible hydrogen for a bulk sample may be below allowable content limits. Localized concentrations of hydrogen often occur more readily in higher strength steels, which have a lower allowable hydrogen content limit, e.g., as low as 1 to 2 ml/100 g. Second, these current standard methods do not lend themselves to nondestructive field or in-place testing of welded joints in components and structures. Therefore, only samples or blanks of welded metal, not actual welds intended for use in machinery, pipelines, and the like, can be measured. Third, once a standard welding procedure is approved with these measuring methods, the welding procedure must be taught and closely followed by every welder. If a welder does not precisely follow the welding procedure due to poor training or other causes, the resulting welded joints in actual machinery, pipelines, or other unacceptable welded objects would not be detectable with these methods, which may leave welded joints intended for use that have undetected hydrogen concentrations above the allowable limits and may fail catastrophically. Fourth, these methods are expensive and time consuming. Delays of at least 24 hours for chromatography testing and delays of at least 72 hours for mercury displacement testing are common.

Some efforts have been made to develop sensors for other applications that detect the presence of hydrogen but are not useful in measuring the concentration of hydrogen. These sensors utilize chemochromic reaction, i.e., a reaction causing optical properties to be altered when certain transition metal oxides are exposed to hydrogen. For example, U.S. Pat. No. 5,708,735 issued to Benson et al. discloses a hydrogen leak detector for hydrogen fuel tanks, which can be placed near the hydrogen fuel tank to monitor the space near the hydrogen fuel tank for the presence of hydrogen. The patented Benson et al. hydrogen leak detector transmits an alarm signal when hydrogen is detected in the space. The detector includes a sensor having an optical fiber with a beveled, three-faceted end that is coated first with a conductive metal (gold or silver) and then a transition metal oxide, such as tungsten oxide. A catalyst material is applied to the metal oxide to quicken the reaction with hydrogen, and finally, a polymer layer is applied over the catalyst to provide a barrier against contaminants. The order and the materials in these layers and the use of a beveled end were selected to produce a detector that utilizes guided wave resonance phenomenon to increase the sensitivity and quickness of hydrogen detection. Resonance occurs when light from an included white light source passes along the optical fiber and strikes the metal-coated, faceted end at an angle just above the critical angle for total internal reflection. The evanescent wave stimulates resonant absorption of the light by free electrons in the metal to produce a surface-plasmon. The layer of transition metal oxide, i.e., chemochromic material, provides an optical wave-guide for light at the surface-plasmon resonance. The layered coating produces a coupled resonance at the surface-plasmon wavelength that is very sensitive to the optical constants of the transition metal oxide layer. When hydrogen reacts with the metal oxide, the resonance frequency shifts, and this shift is detected by a monitoring device that analyzes the spectrum of the reflected beam and an alarm signal is transmitted. While providing initial detection of the presence of a small amount of hydrogen in the general volume surrounding the sensor, this leak detector is not useful for accurately measuring diffusible hydrogen concentrations in a material sample for identifying potential hydrogen damage.

Consequently, a nondestructive, yet accurate, method and device for measuring concentrations of diffusible hydrogen quickly at various locations on material samples, e.g., along the length of a welded joint on a machine, pipeline, or other article that is intended to be placed into use, would be useful to and well-received by the construction, fabrication, and related industries. Further, such a method and device would preferably provide other advantages over the current equipment intensive laboratory tests, such as being portable, inexpensive, and easy to use, to assist industries in more readily meeting quality assurance and safety requirements and standards.

DISCLOSURE OF INVENTION

Accordingly, it is a general object of the present invention to provide an improved method and apparatus for use in measuring diffusible hydrogen concentrations, i.e., volume of hydrogen per unit mass, in an object and/or structure.

It is a more specific object of the present invention to provide a portable, easy-to-use method and apparatus for use in performing field or on-site diffusible hydrogen concentration measurements on an object and/or structure.

It is another specific object of the present invention to provide a method and apparatus for use in measuring diffusible hydrogen concentrations in an object and/or structure in a nondestructive manner.

It is still another specific object of the present invention to provide a method and apparatus for use in measuring diffusible hydrogen concentration distributions in an object and/or structure, e.g., diffusible hydrogen concentrations at various different locations along the length of a welded joint.

It is yet another specific object of the present invention to provide a reliable and accurate method and apparatus for use in measuring diffusible hydrogen concentrations in an object and/or structure in less time than is currently possible.

Additional objects, advantages, and novel features of the invention are set forth in part in the description that follows and will become apparent to those skilled in the art upon examination of the following description and figures or may be learned by practicing the invention.

To achieve at least one of the foregoing objects, as embodied and broadly described herein, the apparatus for use in measuring diffusible hydrogen concentrations includes a portable and readily mounted, sensor assembly having a sensor for positioning an optical fiber with a hydrogen sensing layer and a reflector layer adjacent an object or structure to be sampled for diffusible hydrogen concentrations. The sensing layer is fabricated from a chemochromic material that, when reacted with hydrogen, undergoes a detectable and measurable change in its properties, e.g., optical properties. The reflector layer can be fabricated from a material that reflects incident light passing through the sensing layer and that also acts as a catalyst for quickening the hydrogen reaction in the sensing layer. The measuring apparatus can further include a sensor housing that houses the sensor assembly and provides an inlet for hydrogen to the sensing and reflector layers. The sensor housing is preferably coupled to a sealing member of resilient material that provides a sealing surface on the sample surface and defines a sample area on the sample surface from which diffusing hydrogen is measured, and further, the internal surfaces of the sensor housing and the sealing member define a sample volume for use in determining the concentration of hydrogen. A connector is included to couple an optical fiber, for transmitting light to and from the sensing and reflector layers, to the sensor. The optical fiber is connected at a distal end to a hydrogen monitoring assembly, which includes a light source for transmitting light of a known power and wavelength into the optical fiber and a detector for receiving light reflected from the reflector layer of the sensor assembly. A signal analyzer is linked to the detector and is adapted for calculating the amount of signal drop to determine the diffusible hydrogen concentration in the sampled object, and for welded joints, correlating such measured concentration to the initial diffusible hydrogen concentration.

To achieve at least one of the foregoing objects, the present invention comprises a method of determining diffusible hydrogen concentrations in an object or structure, and particularly, at specific locations along a welded joint. The method includes calibrating a sensor to account for a sample area and sample volume defined by the sensor assembly and for sensor assembly responsivity which is based, at least in part, on the thicknesses and materials selected for the sensing and reflector layers at the end of the optical fiber portion of the sensor assembly. If a welded joint is being sampled, the welded joint is allowed to cool to a temperature suitable for the materials of the measuring apparatus and the elapsed time since completion of the weld is inputted into the signal analyzer for later use in correlating measured hydrogen concentration to initial diffusible hydrogen concentration. The sensor assembly is then mounted on an object or structure to be sampled with a mounting device for compressing the sealing member against the sample surface to obtain a tight seal. The sensing layer of the sensor assembly is allowed to react with hydrogen evolving from the sample surface for a predetermined sample period as to reach a relatively steady-state in the chemical reaction between the sensing layer and the diffusing hydrogen. The sample period is generally 10 to 30 minutes and depends on the design of the sensing and reflector layers and corresponds to the calibrated inputs of the measuring device. The signal analyzer is then operated to determine, and display, the diffusible hydrogen concentration by correlating the calculated drop in signal intensity, i.e., difference in detected intensity between transmitted and reflected light, detected by the detector of the hydrogen monitoring assembly, and in a welded joint application, the signal analyzer can be operated to determine the initial diffusible hydrogen concentration based on such calculated hydrogen concentration, the elapsed time since welding, and the calibrated sensor responsivity.

One embodiment of an apparatus for use in measuring diffusible hydrogen concentrations in an object or structure includes a housing with a first opening that is capable of being operatively connected to the objector structure so as to substantially prevent the diffusible hydrogen coming from the object or structure from escaping during a measurement. The apparatus further includes a hydrogen sensor that is mounted in the housing so as to be exposed to the hydrogen contained by the housing during a measurement. In one embodiment, the optical properties of the sensor change in accordance with changes in hydrogen concentration. When the apparatus is in use, the housing defines the sample area from which diffusible hydrogen is expected to emanate. The housing further defines a sample volume. The sample area, sample volume, and output of the sensor are used to calculate a diffusible hydrogen concentration.

BRIEF DESCRIPTION OF THE DRAWINGS

The accompanying drawings, which are incorporated in and form a part of the specification, illustrate the preferred embodiments of the present invention, and together with the descriptions serve to explain the principles of the invention.

In the Drawings.

BEST MODE FOR CARRYING OUT THE INVENTION

Figure 1:
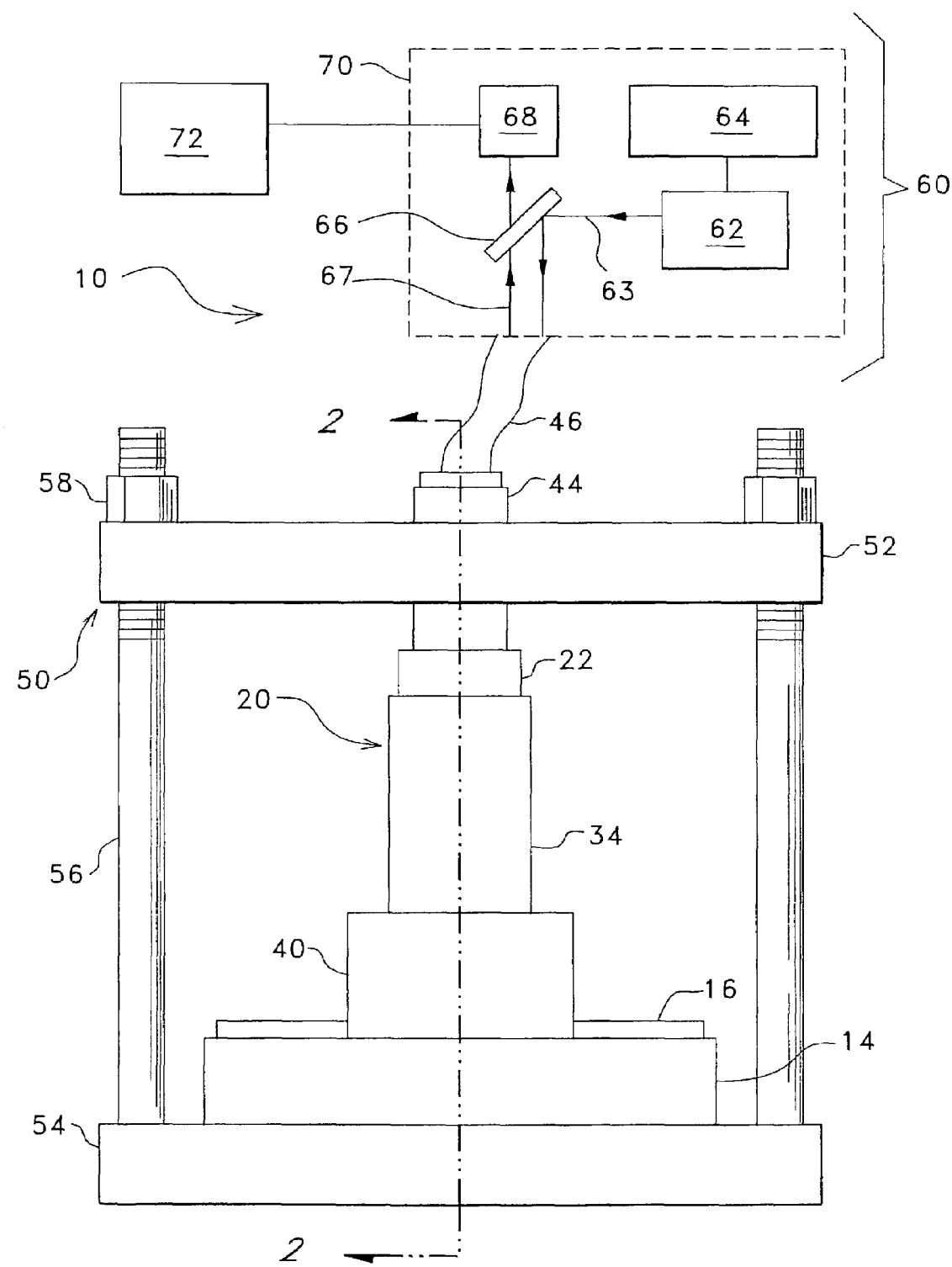
FIG. 1 is an elevation view of a diffusible hydrogen measuring apparatus of the present invention including a block diagram of a hydrogen monitoring portion of the measuring apparatus.

A diffusible hydrogen measuring apparatus 10 for use in measuring diffusible hydrogen concentrations according to the present invention is illustrated in FIG. 1 mounted with a mounting device 50 on a welded object 14 comprising pieces of steel joined with weld bead 16 from a standard arc welding process. Although the present invention is useful for measuring diffusible hydrogen concentration in many structures, such as cannon barrels, pressure vessels, and galvanically protected metal structures, the following description will generally be directed to welded structures, and specifically, welded joints on steel structures, to more fully and clearly describe the inventive features of the present invention. Persons skilled in the art will, upon understanding this description, recognize the applicability of the invention for use on such other structures and will be able to apply this invention for such uses.

Figure 2:
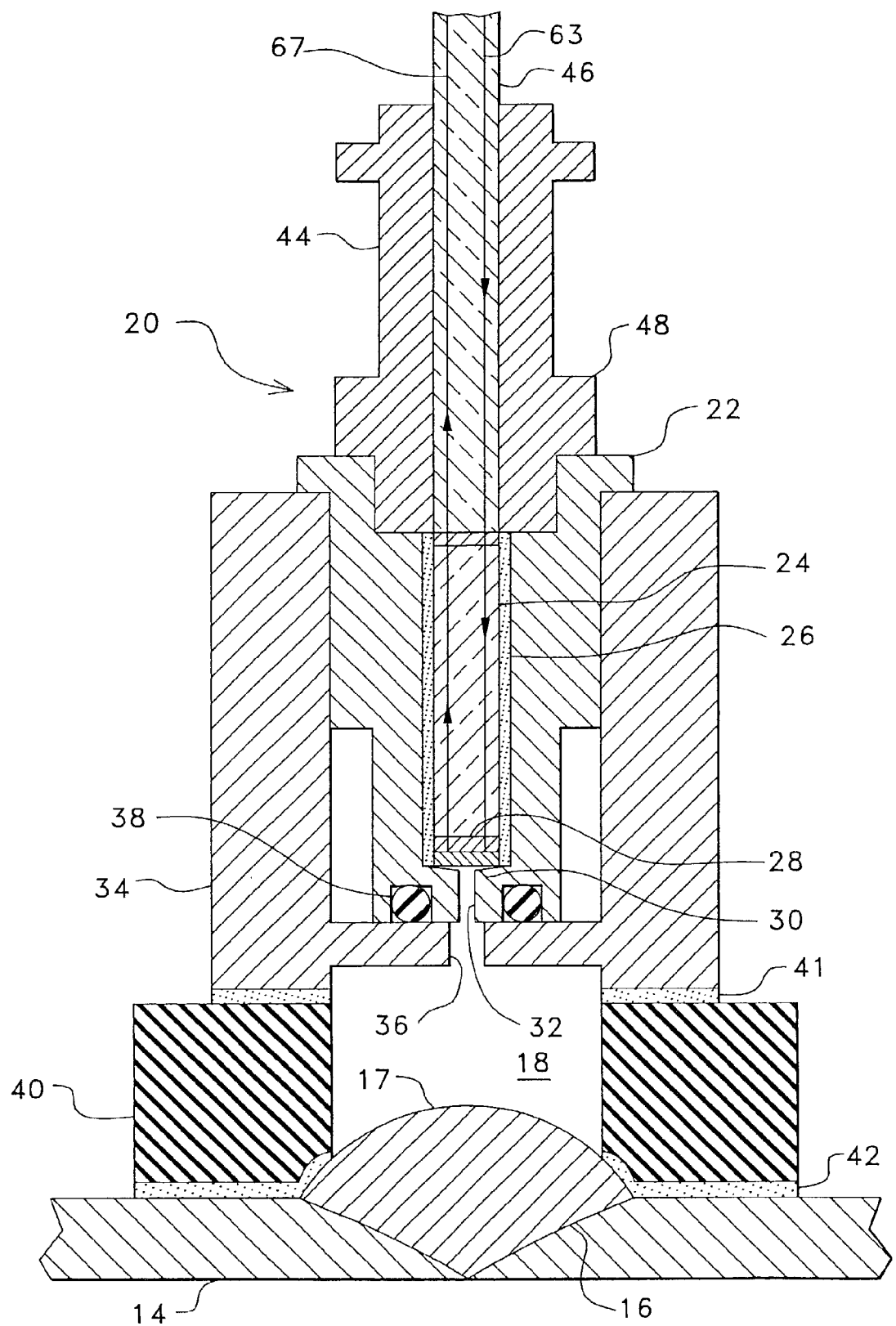
FIG. 2 is a partial cross-sectional view of a sensor assembly portion of the measuring apparatus shown in FIG. 1 taken along line 2-2.

The hydrogen measuring device 10 includes a sensor assembly 20 that functions to define a sample area 17 on a weld bead 16, with a sealing member 40 on the welded object 14, from which hydrogen is allowed to evolve into, and be contained within, a sample volume 18 defined by the sealing member 40, a sensor housing 34, and sensor 22, as illustrated in FIGS. 1 and 2. The evolved hydrogen reacts with a sensing layer 28 and a reflector layer 30 on the end of an optical fiber 24, which is sealably positioned within a sensor 22. The sensing layer 28 comprises a chemochromic material, such as tungsten trioxide, that undergoes changes in physical properties, e.g., such as optical transmission properties, which can be measured to determine the amount of hydrogen evolving from the surface area 17 and reacting with the sensing layer 28. A length of optical fiber 46 is joined to the sensor optical fiber 24 with a connector 48 to direct light 63 transmitted by a light source 62 in a hydrogen monitoring assembly 60 through the sensing layer 28 to strike the reflector layer 30 which reflects light 67 back through optical fiber 46 to a detector 68 in the hydrogen monitoring assembly 60. A signal analyzer 72 is included in the hydrogen monitoring assembly 60 and can be calibrated and configured to provide a measurement of the diffusible hydrogen concentration in the weld bead 16 at the current mounting position along the welded object 14 based on a predetermined responsivity of the sensor assembly 20 and any measured change in the optical properties of the sensing layer 28. In general, the measuring apparatus 10 measures decreases in intensity of light between the transmitted and reflected light, 63 and 67, respectively, that are caused by changes in the optical properties of the sensing layer 28 as it reacts with the evolving hydrogen. As will be discussed in detail below, the measuring apparatus 10 can then be operated to correlate these measured intensity decreases to a quantity of hydrogen in the known sample volume 18 and to then correlate such a calculated quantity of hydrogen to a diffusible hydrogen concentration in portion of the weld bead 16 sampled, i.e., as defined by the sample area 17. In this manner, the hydrogen measuring apparatus 10 is useful for quick and reliable field testing to measure diffusible hydrogen concentrations in a weld bead 16.

According to one aspect of the present invention, the hydrogen concentration measuring apparatus 10 includes a sensor assembly 20 that provides a tight sealing surface between the sensor assembly 20 and a surface on the weld bead 16 on the welded object 14 while also defining the sample area 17 on the weld bead 16 from which hydrogen can evolve into the enclosed sample volume 18 within the sensor assembly 20. As can be appreciated, the accuracy of the measuring apparatus 10 is dependent on minimizing leakage of hydrogen in or out of the sensor assembly 20. To control leakage, the sensor assembly 20 includes sealing member 40 fabricated from a resilient gasket material, such as closed-cell sponge-type rubber, that when compressed or forced against the welded object 14 and against the weld bead 16 provides excellent sealing against hydrogen leakage. A compressible material for the sealing member 40 is preferable because it tends to conform to relatively rough surface areas usually present in welding applications. As illustrated in FIG. 2, a sealant 42, such as high vacuum grease or the like, can be applied to the bottom surface of the sealing member 40 to establish an even more reliable gas seal between the rough surface of the welded object 14 and weld bead 16 and the sensor assembly 20. The sealing member 40 is sealably attached to the sensor housing 34 with a sealant 41. The sealant 41 can be any of a number of well-known sealant materials, and in one embodiment, is an adhesive selected to sealably and securely bond the sealing member 40 fabricated from rubber to the metallic material, e.g., aluminum, of the sensor housing 34.

The sealing member 40 also defines the sample area 17 on the weld bead 16 and, in combination with sensor housing 34, defines the sample volume 18 in which hydrogen evolving from the sensor volume 18 is entrapped for sampling or measurement. Defining a specific sample area, such as sample area 17, allows the amount of material being sampled to be determined, through known geometric and mass calculations based on the weld metals and weld processes employed, as will be described in more detail below. Determination of the quantity of weld material being sampled is desirable because the hydrogen concentration determinations made by the measuring apparatus 10 are preferably expressed in units that comply with standard industry practice, i.e., concentrations in parts per million (ppm) or milliliters of hydrogen per 100 grams of weld or bead metal. By defining a specific sample area 17 on the weld bead 16, the sensor assembly 20 is useful for measuring diffusible hydrogen concentrations along the weld bead 16. As explained above, highly concentrated pockets of hydrogen can cause or initiate hydrogen damage, such as cracking, but, these pockets of high concentrations are often not detectable by standard hydrogen tests that measure hydrogen evolving from a larger weld sample or coupon. To alleviate these problems with standard hydrogen tests, measuring apparatus 10 can be readily moved along a weld bead 16 to develop a diffusible hydrogen concentration distribution (i.e., hydrogen concentration measurements along a given length or about a surface area of a weld rather than only at one point) to improve safety and quality assurance of welding processes or a plurality of sensor assemblies 20 can be deployed along the length of the weld bead 16 (an alternate embodiment of a measuring apparatus 10 not shown but described in more detail below).

The internal shape of the sealing member 40 can be selected from a large number of shapes. In the illustrated embodiment of FIG. 2, the internal shape of the sealing member 40 is cylindrical, which defines a substantially circular sample area 17 from which diffusible hydrogen can evolve into the sample volume 18. Because it is generally preferable that samples are only taken from the weld material to improve the accuracy of the measuring apparatus 10 by increasing the hydrogen diffusion rate per surface area sampled, the size, i.e., the diameter, of the internal shape of the sealing member 40 is can be varied to suit the width of the weld bead 16 and selected to be slightly less than such width. As illustrated, the internal shape of the sealing member 40 may have a diameter ranging from, for example, but not for limitation, ¼ to ¾ inch. This cylindrical shape of sealing member 40 along with the bottom internal surfaces of the sensor housing 34 and the sensor 22 defines the sample volume 18. While the sample volume 18 can be varied in practicing the invention by altering the size and configuration of the sensor assembly 20, the sensor assembly 20 is calibrated and a response curve determined based on a specific and known sample volume 18, as will be described in more detail below. If changes are made to the size or configuration of the portions of the sensor assembly 20 (i.e., the sensor 22, the sensor housing 34, and the sealing member 40) that define the volume 18, the sensor assembly 20 can be recalibrated to account for any corresponding changes in the sample volume 18.

In an alternate embodiment, a gas-tight seal may be obtained between the sensor housing 34 and the welded object and weld bead 14 and 16, respectively, by use of a moldable and adhesive material, such as a putty material, for the sealing member 40. A moldable material for the sealing member 40 would be useful because it would tend to mold or fill into irregularities on the surface of the weld bead 16 and would also provide bonding with the sensor housing 34, the welded object 14, and the weld bead 16, thereby reducing or eliminating the need for sealant 41 and 42. Because the sample area 17 and sample volume 18 may vary with each use or application of the sensor assembly 20, the use of a putty-type substance for the sealing member 40 would require the user of the measuring apparatus 10 to calculate and/or measure the sample area 17 and the sample volume 18 in the field. The hydrogen monitoring assembly 60 could then be configured to accept, e.g., as user input, these calculated values of sample area 17 and sample volume 18 for use in determining the diffusible hydrogen concentration in the weld bead 16.

According to another important aspect of the present invention, the measuring apparatus 10 includes a hydrogen sensing layer 28 that is fabricated from a material that chemically reacts with atomic hydrogen, and as a result of the chemical reaction, certain electrical (e.g., specific resistivity) and/or optical (e.g., dielectric or transmissivity) properties of the sensing layer 28 change as a function of the quantity of hydrogen reacting with the sensing layer 28. By accurately measuring select changes in the properties of the sensing layer 28 material and with the known sample area 17 and sample volume 18, the diffusible hydrogen concentration in the weld bead 16 can be determined. For example, the change in resistivity of the sensing layer 28 could be determined by connecting a voltage source(s) (not shown) to the sensing layer 28 at one or more points on the sensing layer 28 and measuring the current flowing through the sensing layer 28. The sensor assembly 20 could be calibrated such that for a given sensing layer 28 material and thickness a calculated change in resistivity would be correlated to a diffusible hydrogen concentration.

In the embodiment illustrated in FIGS. 1 and 2, the measuring apparatus 10 is operable to measure diffusible hydrogen concentrations by first measuring changes in the optical transmission properties of the sensing layer 28 in response to exposure of the sensing layer 28 to hydrogen evolving from the surface area 17 on weld bead 16 and captured in the volume 18 defined by the sensor assembly 20. The measuring apparatus 10 then uses these measured changes to calculate volumes of hydrogen evolving from the sample area 17 in a manner that will be described below. A number of chemochromic materials can be utilized to practice the present invention. For instance, the chemochromic reactions, and thus changes in electrical or optical properties, of transition metal oxides, such as tungsten trioxide ($WO_3$), molybdenum trioxide, and rare earth and lanthanide dihydrides (e.g., yttrium dihydride and lanthanum dihydride) with hydrogen are particularly well-suited for measuring the concentration of hydrogen, because the chemical reaction can be closely monitored with electrical or optical measuring techniques and is also reversible, thereby making the sensing layer 28 useful for repeated use. The number of uses that a sensing layer 28 can be used may vary based on the chemical characteristics of the material(s) selected for the sensing layer 28 because the reversibility and the sensitivity of the sensing layer 28 to hydrogen may vary with age and the number of previous uses. The number of uses may be extended by incorporating correction factors into the measuring apparatus 10 to account for any predictable changes in the sensing layer 28.

In one embodiment, the sensing layer 28 comprises a thin, e.g., 500 nanometers in thickness, film of $WO_3$ coated on the end of a section of optical fiber 24, e.g., 4.7 millimeter polymer optical fiber. During operation of the measuring apparatus 10, transmitted light 63 is guided through the optical fiber 24 to contact the sensing layer 28 and to allow changes in the optical transmission properties of the sensing layer 28 to be measured. The optical fiber 24 is centrally positioned within a sensor 22 which is held within the sensor housing 34 by standard fastening means. In one preferred embodiment, the sensor 22 is externally threaded and can be screwed into the sensor housing which contains internal threading, thus allowing reuse of the sensor housing 34 with ready replacement of the sensor 22, including the sensing layer 28, with a new, calibrated unit. A resilient member 38, such as a standard o-ring as illustrated in FIG. 2, is included in the sensor assembly 20 to provide sealing between the sensor 22 and the sensor housing 34 to minimize hydrogen leakage from the sample volume 18. The optical fiber 24 is sealed and fixed within the sensor 22 with a fiber sealant 26 suitable for the exterior material of the optical fiber 24 and the interior material of the sensor 22, e.g., metals such as aluminum or plastics, and in one embodiment, paraffin wax is used for the fiber sealant 26 to obtain an acceptable, gas-tight seal between the optical fiber 24 and the sensor 22.

The sensing layer 28 may be fabricated or coated onto the end of the optical fiber 24 by a number of thin film fabrication techniques that provide good bonding to the optical fiber 24 and are capable of achieving acceptable tolerances in the preferred thickness ranges of the present invention. For example, but not as a limitation, the sensing layer 28 may be applied to the optical fiber 24 using chemical vapor deposition, evaporative deposition, anodic deposition, reactive sputtering, photochemical vapor deposition, sol-gel processes, or electron beam deposition. In a preferred embodiment, the sensing layer 28 is fabricated utilizing evaporative deposition because a porous, low-density film is attained that is desirable for hydrogen measurements because it allows hydrogen to more readily penetrate the sensing layer 28 to chemically react with the material of the sensing layer 28.

According to another important aspect of the present invention, the measuring apparatus 10 is designed to provide an accurate measurement of diffusible hydrogen concentration with significantly improved speed. Standard industry practices require a weld coupon to be shipped to a laboratory and, generally, tested for a 72-hour period. In contrast, the measuring apparatus 10 includes a number of innovative features that enable it to determine diffusible hydrogen concentration in a welded joint within minutes. For example, once the weld has cooled to a temperature that will not deteriorate the materials of the sensor assembly 20, the sensor assembly 20 can be mounted on a welded object 14 and determine the hydrogen concentration in a time period typically ranging from 10 to 30 minutes but depending on the size and thickness of the sample volume 18 and the sensing layer 28. In this regard, the sampling volume 18 is preferably maintained relatively small, e.g., 2 milliliters, so as to more quickly elevate the amount of evolved hydrogen within the sampling volume 18 and bring the evolved hydrogen into contact with the sensing layer 28.

To further improve the quickness or timeliness of the measuring apparatus 10, a reflector layer 30 is positioned on top of the sensing layer 28 that functions as a reflecting device and also as a catalyst for the hydrogen reaction with the sensing layer 28. To enable measurement in changes in the optical transmission properties of the sensing layer 28, the reflector layer 30 is preferably fabricated from a material that can reflect substantially all the transmitted light 63 which is transmitted through the sensing layer 28 as reflected light 67 having a measurable reflected intensity, typically measured in nanowatts. Of course, the reflected light 67 will have an intensity that is less than the transmitted light 63 because of attenuation by the sensing layer 28 of the transmitted light 63 (both as it passes down through the sensing layer 28 to the reflector layer 30 and as it passes back up through the sensing layer 28), with increases in the level of attenuation being measured to identify changes in the optical transmission properties of the sensing layer 28. Further, the reflector layer 30 is a planar surface that is substantially perpendicular to the axis of the optical fiber 24 to reflect the light 67 back through the sensing layer 28. Additionally, the reflector layer 30 is preferably fabricated from a material that allows evolving hydrogen to not only pass through the reflector layer 30 to reach the sensing layer 28 but to speed up the resulting chemical reaction. Both of these functions may be achieved by a thin film of a number of metals including, but not limited to, palladium and platinum, that reflect incident light beams and also act as catalysts by adsorbing molecular hydrogen on the surface of the reflector layer 30, converting the adsorbed hydrogen into atomic hydrogen (which is more reactive with transition metal oxides), and releases the atomic hydrogen into the sensing layer 28. In a preferred embodiment, the reflector layer 30 comprises a palladium film with a thickness in the range of 3 to 30 nanometers applied to the sensing layer 28 with one of the thin film fabrication processes discussed for fabrication of the sensing layer 28.

During operation of the measuring apparatus 10, hydrogen evolves from the sample area 17 into the sample volume 18 and then naturally rises up through hydrogen inlet 36 in the sensor housing 34 and aperture 32 in the sensor 22 to contact the reflector layer 30. The reversible, chemical reaction that occurs between the evolving hydrogen and the reflector and sensing layers 30 and 28, respectively, can be represented by the following equation:

$$\mathrm{Pd} + x\mathrm{H}_2 + x/4\mathrm{O}_2 + \mathrm{WO}_3 \longleftrightarrow \mathrm{H}x\mathrm{WO}_3 + x/2\mathrm{H}_2\mathrm{O} + \mathrm{Pd}$$

The hydrogen reacts reversibly to form a hydrogen tungsten bronze in the sensing layer 28 in which optical absorption occurs, i.e., the optical transmission rate for the sensing layer 28 material is decreased, by electrons undergoing intervalence transfer. The transferred electrons can be visualized as electrons trapped in distorted lattice sites and are generally considered to be the cause of the chemochromic effects which the present invention uses to measure the diffusible hydrogen content in the weld bead 16. In practice, the reversibility of the reaction may be compromised, thereby requiring occasional replacements of the sensing layer 28.

The sensor assembly 20 includes optical fiber 46 through which light 63, 67 can be transmitted to and from the optical fiber 24 and sensing layer 28 in the sensor 22. A standard optical fiber connector 44 is used to provide mechanical connection of the optical fiber 46 to the sensor 22 and to provide abutting contact between optical fibers 24 and 46. Since optical fiber connectors 44 are typically provided with male threaded ends, the sensor 22 can be fabricated with a female threaded end to receive the connector 44. As illustrated in FIG. 2, a fiber coupler 48, such as an index match gel, can be included to reduce any losses in light intensity or power at the interface between the two optical fibers 24, 46.

The measuring apparatus 10 of the present invention is useful for monitoring changes in the optical transmission properties of the sensing layer 28, using these property changes to measure the concentrations of hydrogen evolving from a sample surface, correlating these hydrogen concentrations to volumetric quantities of hydrogen in the sample, e.g., milliliters of hydrogen per 100 grams of weld metal. To achieve these varied functions, the measuring apparatus 10 includes a hydrogen monitoring assembly 60 that is connected to the optical fiber 46 for inputting light 63 to and receiving, and analyzing, reflected light 67 from the sensor assembly 20. The hydrogen monitoring assembly 60 includes a light source 62 powered by power source 64, i.e., a battery or the like. Because light over a broad spectrum can be used to detect optical transmission changes in the sensing layer 28, the light source 62 may include any of a number of known devices, such as, for example, a light emitting diode (LED) for transmitting a broad spectrum white light or a LED for transmitting infrared (IR) light of a known wavelength. It may also be desirable that the light source 62 transmit light 63 as collimated rather than diverging bundles of light rays and the light source 62 may include a collimating device. In a preferred embodiment, the light source 62 is a laser emitting light 63 at a wavelength of 850 nanometers at an intensity in the 1 to 3 micro watt ($\mu$W) range.

The hydrogen monitoring apparatus 60 may include a beam splitter 66 for directing the transmitted light 63 into the optical fiber 46. The beam splitter 66 also initially receives the reflected light 67 from the optical fiber 46 and directs it to a detector 68. The detector 68 functions to measure the intensity of the reflected light 67 and may be a phototransistor that transmits an electrical output proportional to the detected intensity or power in the reflected light 67. As illustrated in FIG. 1, the light source 62, the power source 64, the beam splitter 66, and the detector 68 may be combined into a single reflectance measuring device 70, such as an infrared reflectometer, to provide portability and ease of use. Generally, it is preferable that the reflectance measuring device 70 be adapted for providing real-time display of reflectance measurements and for providing output to peripheral components for further analysis and manipulation of measured reflected light 67 intensities. Testing has shown that a $WO_3$ sensing layer 28 can act as a highly hydrogen-sensitive detector, reacting to a mixture of one percent hydrogen in argon within minutes with a decrease in reflectance of approximately 80 percent.

Figure 3:
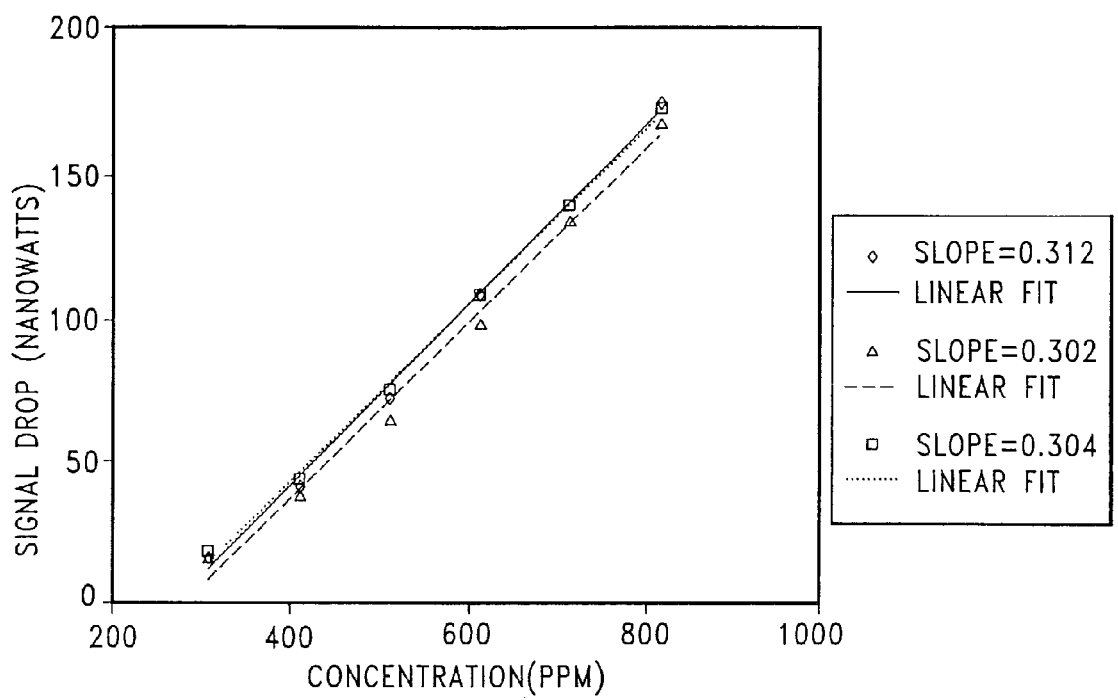
FIG. 3 is a graph illustrating hydrogen calibration curves for a sensor according to the present invention having a tungsten oxide sensing layer and a palladium catalyst layer.

According to another important aspect of the present invention, the measured changes in optical properties are correlated to concentrations of hydrogen and then used to quantify the volume of diffusible hydrogen in a particular sampled mass. In general, the measuring apparatus 10 is calibrated to first correlate a detected optical change (visible as a color change) in the sensing layer 28 to a concentration (ppm) of hydrogen in the sample volume. As illustrated in FIG. 3, a linear sensor response or correlation was found for a $WO_3$ sensing layer 28 with a palladium layer 30 between the increase in hydrogen concentration and decrease in reflectance intensity, i.e., signal drop in nanowatts. The linear correlation of FIG. 3 was developed by exposing a $WO_3$ sensing layer 28 and a reflector layer 30 to known quantities of hydrogen in a controlled atmosphere, i.e., synthetic air of 80% nitrogen and 20% oxygen, having a volume of approximately 0.5 liters. The sensing and reflector layers 28 and 30 were allowed to react for fifteen minutes with each hydrogen concentration (ppm), and a reflectometer was used to measure the signal drop. The response of the sensing layer 28 was found to be linear over a wide range of hydrogen concentrations, and specifically, a linear response was found when hydrogen concentrations ranged from 200 to 1000 ppm in the controlled volume. The calibration data was then converted to volumes of hydrogen ($\mu$liters) and then adjusted for the differences in calibration volume (0.5 liters, as discussed above) and sample volumes 18 of the sensor assembly 20 by multiplying the volume of hydrogen by the ratio of the sensor volume 18 to that of the calibration volume. This adjusted volume was then plotted (not shown) as a function of sensor response, i.e., signal drop, to correlate the volume of diffusible hydrogen to the signal drop detected in the sensor 28, a curve with a slope with units of $\mu$liter/nW. Significantly, the slope of this curve provides a standard conversion factor that can be applied to each sensor assembly response curve acquired from a weld material to determine a rate of diffusivity from the weld material, i.e., in units of $\mu$liter/minute, which, in turn, can be used to determine the initial diffusible hydrogen concentration in a weld sample.

Significantly, the predictable, linear response of the sensing layer 28 and reflector layer 30 enables the sensor assembly 20 to be calibrated for determining the diffusible hydrogen in a weld sample and, further, for determining the initial diffusible hydrogen concentration in the weld sample, i.e., in the weld material. In this regard, the inventors performed a series of experiments that correlate the slope of a sensor response curve to the initial diffusible hydrogen concentration in a weld sample, such as weld bead 16. The steady state portion of a sensor response curve was assumed to be proportional to the flux, e.g., diffusivity rate, of hydrogen from the weld sample, which in turn is proportional to the initial concentration of hydrogen in the weld sample. Slopes of curves generated with the sensor assembly 20 using welded samples were found to correlate closely with quantitative results for initial diffusible hydrogen concentrations in duplicate welded samples that were analyzed using a standard method, i.e., AWS A4.3-93, for measuring diffusible hydrogen concentrations. The slopes of the generated curves from the sensor assembly 20 also closely correlated with curves developed from a theoretical diffusion equation, based on a form of the error function equation.

Figure 4:
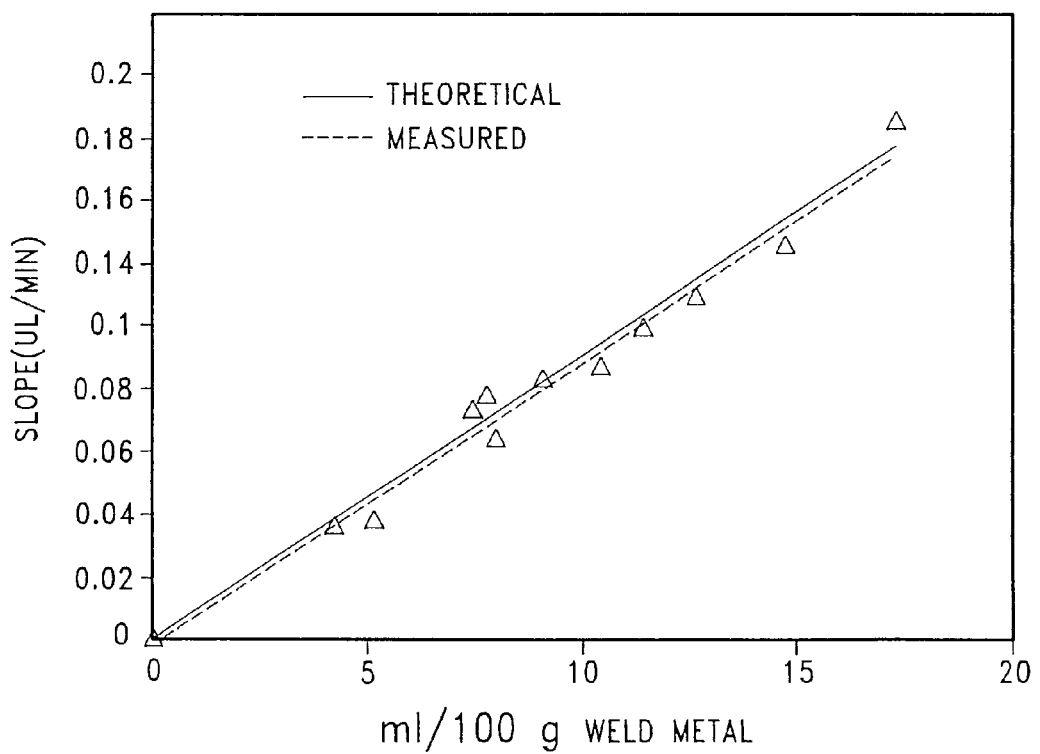
FIG. 4 is a graph illustrating a comparison of experimental and theoretical data for a diffusible hydrogen measuring apparatus of the present invention with weld samples from a gas metal arc welding process on HSLA 100 Steel and with a diffusion coefficient of $7.5 \times 10^{-5}$ cm$^2$/second.

More specifically and with reference to FIG. 4, solutions for the theoretical diffusion equation were generated for different initial diffusible hydrogen concentrations as a function of time with the results being adjusted for the average amount of weld metal per sample and multiplied by the ratio of surface area sampled, i.e., sample area 17, to total area of the welded object. The slopes of theoretical curves resulting from the equation solutions were calculated in 2 hour time intervals in units of $\mu$liter/minute based on weld samples from gas metal arc welding of HSLA 100 steel.

Using the sensor assembly 20, response curves were then developed for a number of weld samples, the slopes of the response curves were determined, and the slopes were converted to units of $\mu$liter/minute, as described above. FIG. 4 illustrates the close correlation between the expected theoretical diffusible hydrogen concentrations and the diffusible hydrogen concentrations measured during use of the sensor assembly 20.

As can be appreciated, the present invention is useful for quickly determining a response curve slope from concentrations of diffusible hydrogen evolving from a welded surface into the sample volume that is indicative of hydrogen diffusivity rate, and then relating such slope back to the initial diffusible hydrogen concentration existing in the weld material immediately after weld completion according to the slopes of curves generated experimentally and/or theoretically, which, as explained above, correlated closely with initial diffusible hydrogen concentrations in duplicate welds, i.e., welds made with the same kinds of materials in the same conditions.

The hydrogen monitoring assembly 60 can be configured to store all of the calibration data for a particular sensor assembly 20 design, to store data collected by the detector 68 during operation of the measuring apparatus 10, and to apply the calibration data to the collected data to determine (automatically or on demand) diffusible hydrogen concentrations. In this regard, the hydrogen monitoring assembly 60 includes a signal analyzer 72 that is communicatively linked to the detector 68. The signal analyzer 72 may be a data processing device or computer, e.g., a personal or laptop computer, that can be programmed to perform calculations to convert measured decreases in the intensity of the reflected light 67 into hydrogen concentrations in the weld bead 16 and into initial diffusible hydrogen concentrations in the weld bead 16. Optionally, the signal analyzer 72 should be programmable to produce and display calibration, sensor response, and other pertinent curves or graphs. Additionally, the signal analyzer 72 preferably includes a data interface, e.g., a general purpose instrument bus (GPIB), that is compatible to the reflectance measuring device 70 and a monitor portion for displaying generated data and/or curves. Alternately, the signal analyzer 72 may be incorporated, by using a microprocessor or similar device, into the reflectance measuring device 70 to provide a more portable and compact hydrogen monitoring assembly 60.

To mount the sensor assembly 20 onto a welded object 14, the measuring apparatus 10 includes a mounting device 50. In addition to providing a means of temporarily (for the length of the sample period) attaching the sensor assembly 20, the mounting device 50 functions to apply an equally distributed compressive force on the sealing member 40 to achieve a gas-tight seal with the welded object 14. As illustrated in FIG. 1, the mounting device 50 includes a top plate 52 with a hole for receiving the connector 44 (prior to attachment of the optical fiber 46) and a bottom plate 54 for contacting the underside of the welded object 14. The top plate 52 applies a force substantially equally to the connector 44 when fasteners 58, i.e., nuts, are tightened on threaded rods 56. The plates 52, 54 can be fabricated from a wide variety of materials, such as plastics and metals, and can be formed in a myriad of shapes, such as circles, squares, and triangles. A plurality of threaded rods 56 preferably are included and equally spaced on the periphery of the plates 52, 54 to equally distribute the compressive forces on the sealing member 40. Similarly, the tightening of the fasteners 58 should be performed in acceptable patterns to obtain relatively equal crush in the sealing member 40, such as patterns used for obtaining proper gasket crush in bolted joints. Other devices for establishing a sufficient seal between a housing and an object or structure known to those skilled in the art are also feasible for use with the present invention. Among these sealing devices are vacuum and glue devices.

In an alternate embodiment of the present invention (not shown), a hydrogen measuring apparatus is provided that is particularly suited for determining the distribution of hydrogen concentrations along a welded joint. In this embodiment, a number of sensor assemblies, similar to sensor assembly 20, are joined in a fashion that replicates the shape of a welded joint. For example, the sensor assemblies can be joined in a straight line for a welded joint on a relatively flat or horizontal surface or the sensor assemblies can be joined to form an arc or full circle for a curved welded joint, i.e., for sampling welded pipe and the like. A mounting device is included that is adapted for providing substantially equal pressure on each sensor assembly to obtain good sealing surfaces and for mounting on the particular welded object, such as structural objects or piping. A hydrogen monitoring assembly is included to direct light of a known wavelength and intensity to each sensor assembly, to detect changes in reflectance in each sensor assembly, and to determine the diffusible hydrogen concentration (current and initial, in units of milliliter/100 grams of weld material). In this manner, the distribution of diffusible hydrogen concentrations along a welded joint can be quickly and accurately determined.

To further illustrate the present invention, a method of preparing and operating the measuring apparatus 10 is described below. Prior to operating the measuring apparatus 10, the sensor assembly 20 is fabricated carefully selecting the proper materials and thicknesses for the sensor and reflector layers 28 and 30, respectively, to obtain quick and measurable chemical reactions with hydrogen, as discussed previously in detail. The fabricated sensor assembly 20 is then calibrated with the use of theoretical data and curves, measured sample areas 17 and sample volumes 18 for the particular sensor assembly 20, and actual calibration testing of the sensor assembly 20. The calibration data, including the sensor response data, for the sensor assembly 20 is programmed into the signal analyzer 72, along with intensity and wavelength information for the transmitted light 63 from light source 62. As discussed previously, the signal analyzer 72 is also programmed with conversion factors and equations to be able to process later received calibration data and signal loss information.

Once the sensor assembly 20 is calibrated and the signal analyzer 72 programmed, the sensor assembly 20 can be mounted on a welded object 14. Typically, the weld bead 16 is allowed to cool down to temperatures that will not harm the measuring apparatus 10 or increase worker safety risks. A period of two hours is generally adequate to cool down the weld while not reducing the accuracy of the measuring apparatus 10; preferably, sampling of a welded object 14 is performed within approximately five hours so that the rate of hydrogen evolution is compatible with the sensitivity of the sensing layer 28 material and detector 68. The length of this cool down period is entered into the signal analyzer 72 for later use in calculating the initial diffusible hydrogen concentration in the weld bead 16. The mounting device 50 is then used to clamp the sensor assembly 20 onto the welded object 14, with sealant 42 being applied to the sealing member 40 to achieve a gas-tight seal. The optical fiber 46 is connected to the connector 44 to optically link the hydrogen monitoring assembly 60 and the sensor assembly 20.

Hydrogen is allowed to evolve from the sampling area 17 into the sample volume 18 and react with the sensing and reflector layers 28, 30 for a sampling period. The sample period typically ranges in length from 10 to 30 minutes but may vary significantly depending on the sensor and reflector layer 28 and 30 materials and thicknesses and the sampling volume 18 in a particular sensor assembly 20. The light source 62 then transmits light 63 at a known wavelength and intensity through the optical fibers 46 and 24 to, at least partially, pass through the sensing layer 28 and be transmitted back to the hydrogen monitoring assembly 60 as reflected light 67 by the reflector layer 30. The reflected light 67 is received by the detector 68 which operates to sense the intensity or power in the reflected light 67. The detector 68 transmits a signal to the signal analyzer 72 having a strength proportional to the intensity of the reflected light 67 and concurrently the reflectance monitoring device 70 can operate to display the detected reflectance, i.e., intensity of light 67.

Signal analyzer 72 compares the signal received from the detector 68 to an initial or calibrated reflectance value for the sensor assembly 20 to determine a signal drop in nanowatts. The signal analyzer 72 then operates to correlate the signal drop to a concentration (ppm) of hydrogen, see FIG. 3. With this calculated hydrogen concentration, the signal analyzer 72 next quantifies the concentration with the sample area 17 and sample volume 18 into a volume of hydrogen per sample mass. For example, to comply with welding practices, the signal analyzer 72 will quantify diffusible hydrogen concentration as milliliters of hydrogen per 100 grams of weld material. Further, the signal analyzer 72 functions to use calibration data, such as the sensor response data, to determine the diffusion rate of hydrogen from the sample area 17 to determine the initial diffusible hydrogen concentration in the weld bead 16. To determine distributions of diffusible hydrogen concentrations, the sensor assembly 20 can be moved along the weld bead 16 once the sampling period has expired and sample data has been taken by operation of the hydrogen measuring assembly 60.

In an alternate method of preparing and operating the measuring apparatus 10, internal calibration of the sensor assembly 20 is included to replace the calibration step discussed in the previously discussed method and/or as an additional step such as when a sensor assembly 20 is used more than once. The accuracy of a diffusible hydrogen concentration measurement by the measuring apparatus 10 depends, at least in part, on variations in environmental and component parameters that can occur between each use of the measuring apparatus 10. For example, the temperature of the sensing layer 28 may vary from measurement to measurement depending on the adjacent structures and space and on the length of time a weld bead 16 is allowed to cool. Additionally, the sample volume 18 may vary with each measurement due to irregularities on the weld bead 16 or due to object or structure shapes that vary from the initial calibration shapes. Further, the sensitivity of the sensing layer 28 may change as the material in the sensing layer 28 ages and as the sensing layer 28 reacts with other chemicals or contaminants emanating from the weld bead 16.

Internal calibration is achieved by introducing a precise and known amount of hydrogen into the sample volume 18 before, during, or after the measurement of hydrogen concentrations in the sample volume 18 that have evolved from the weld bead 16 for the determination of diffusible hydrogen concentrations in weld bead 16, as discussed above. For illustration purposes, but not as a limitation, the diffusible hydrogen emanating from the weld bead 16 and captured in the sample volume 18 can first be measured as discussed above and the resulting signal from the detector 68 recorded and/or stored by the signal analyzer 72. Next, a known calibration amount of hydrogen can be injected into the sample volume 18 for in situ calibration of the sensor assembly 20. The sensing layer 28 is allowed to absorb the injected calibration hydrogen for a certain period of time, e.g., 10 to 30 minutes, and then the detector 68 is operated to detect the intensity of the reflected light 67 and to transmit a signal to the signal analyzer 72. The signal analyzer 72 can be programmed to store the incremental or new intensity after the injection of the calibration hydrogen and to determine a ratio of the actual hydrogen concentration signal to the incremental calibration signal. This ratio can then be multiplied by the known volume of injected calibration hydrogen to calculate the volume of the measured hydrogen in sample volume 18. In this manner, the internal calibration step produces more accurate measurements of evolved diffusible hydrogen in the sample volume 18 by accounting for variations in sample volume 18 and in temperature and sensitivity of the sensing layer 28 from one sample measurement to the next.

The injection of a known amount of hydrogen into the sample volume 18 can be accomplished through a number of processes. For example, a small volume of compressed hydrogen may be inserted into the sample volume 18 by breaking a small hydrogen-filled glass sphere (not shown but may be similar to those fabricated for hydrogen gas fuel storage by 3M Corporation and others) within the sensor housing 34. Alternatively, a small amount of hydrogen may be generated inside the sensor housing 34 by passing an electrical current through the sensor housing 34 to heat a small amount of a metal hydride (not shown) positioned within the sensor housing 34. When heated, such metal hydrides release their absorbed hydrogen in a predictable manner. The hydrogen-producing metal hydride may take the form of a fine wire or a thin film or foil so that a small amount of electrical energy is required to heat the metal hydride and release the hydrogen without appreciably altering the temperature of the sensing layer 28. As a further example, a small volume of hydrogen may be injected into the sensor housing 34 by electrically dissociating a small amount of water in an attached container (not shown) in communication with the sample volume 18. The amount of hydrogen released from the stored water is directly proportional to the amount of electrical current passed through an electrolyzer positioned in the water container. The electrolyzer current may be controlled to provide different amounts of calibration hydrogen appropriate for different measurement conditions or to provide a number of varying volumes of hydrogen for insertion into the sensor housing 34 to provide a more thorough internal or in situ calibration of the sensor assembly 20.

The foregoing description is illustrative of the principles of the invention and provides a specific example of the hydrogen concentration measurement concepts of the present invention, and for ease of illustration, use of the invention for in measuring diffusible hydrogen concentrations in and along a weld bead was shown in the attached figures. However, the above discussion should not be limited to the specific example shown but is expressly intended for other types of applications in which the measurement of hydrogen concentrations, such as cannon barrels, pressurized containers, and structural materials subject to pressurized hydrogen or chemical reactions involving hydrogen, can be useful in predicting or determining hydrogen damage.

As can be appreciated from the foregoing description, the present invention provides an apparatus and method for measuring diffusible hydrogen in an object or structure that is fabricated from a material susceptible to hydrogen damage. The present invention is advantageously useful for on-site or field testing of such an object or structure. In this regard, the apparatus of the present invention is portable, readily attachable or mountable to a sample surface, and is easy to operate with minimal training and can provide display and storage of sample results and data. The method of the present invention provides accurate measurements of diffusible hydrogen concentrations in a quick and timely fashion, i.e., a matter of minutes, rather than the hours or days that are common in prior art hydrogen testing procedures. Furthermore, since numerous modifications and changes will readily occur to those skilled in the art, it is not desired to limit the invention to the exact construction and process shown and described above. Accordingly, resort may be made to all suitable modifications and equivalents that fall within the scope of the invention as defined by the claims which follow. The words "comprise," "comprises," "comprising," "include," "including," and "includes" when used in this specification are intended to specify the presence of stated features, integers, components, or steps, but they do not preclude the presence or addition of one or more other features, integers, components, steps, or groups thereof.

What is claimed is:

1. A method for measuring a diffusible hydrogen concentration in an object at a particular previous point in time, comprising:
   selecting a portion of the object from which to obtain a diffusible hydrogen concentration measurement;
   sealably mounting a hydrogen sensor assembly on the selected portion of the object, the sensor assembly including a housing that defines a sample area on the selected portion from which hydrogen is allowed to evolve and a predetermined sample volume in which the evolving hydrogen is captured, wherein the sensor assembly further includes a hydrogen sensor comprising a hydrogen-reactive material mounted within the housing adjacent the sample volume, said hydrogen-reactive material being of a type that has a physical property which changes as a function of hydrogen concentration in the sample volume;
   allowing the hydrogen sensor to react with the captured evolving hydrogen for a sample time period that is at a sampling time subsequent to said previous point in time whereat the rate of hydrogen evolution is compatible with the sensing ability of the hydrogen reactive material;
   measuring change in the physical property of the hydrogen sensor over said sample time period;
   correlating said change via a predetermined relationship between the physical property measured and concentration of hydrogen to obtain a rate of change of hydrogen in the sample volume during the sample period, which corresponds to hydrogen diffusivity rate from the object; and
   determining the diffusible hydrogen concentration in the selected portion of the object at said particular previous point in time based on the rate of change in the physical property of the hydrogen sensor by correlating the rate of change in the physical property via a predetermined relationship between rate of change in the physical property to diffusible hydrogen concentration in the object.

2. The method of claim 1, wherein the sample time period is in a range of 10 to 30 minutes.

3. The method of claim 1, wherein the selected portion is a welded joint, and further including prior to the mounting, waiting a cooling time period after the welded joint is welded, and determining an initial diffusible hydrogen concentration in the welded joint by correlating the hydrogen diffusivity rate at the cooling time with a predetermined example slope from among a plurality of pre-determined example slopes of hydrogen diffusion curves for a plurality of example initial diffusible hydrogen concentrations at said cooling time period.

4. The method of claim 1, wherein the physical property is optical transmissivity of the hydrogen sensor and the sensor assembly further includes a reflector positioned within the housing so as to be interposed between the sample volume and the hydrogen sensor, the reflector being configured for reflecting light passing through the hydrogen sensor back through the hydrogen sensor.

5. The method of claim 4, further including operatively connecting a reflectance monitoring device including a light source and a light signal detector to the sensor assembly, and wherein the measuring includes operating the reflectance monitoring device to transmit a light signal from the light source to the hydrogen sensor and to receive a reflected portion of the light signal with the light signal detector.

6. The method of claim 5, further including connecting a signal analyzer to the light signal detector for receiving a signal from the light signal detector based on the received reflected portion, and wherein the calculating of the diffusible hydrogen concentration is completed in part by operating the signal analyzer to compare the signal from the light signal detector and the transmitted light signal from the light source.

7. The method of claim 1, further including calibrating the hydrogen sensor assembly to create calibrating information, and wherein the calculating of the diffusible hydrogen concentration is based on the calibrating information.

8. The method of claim 7, the calibrating being completed prior to the mounting of the hydrogen sensor assembly based on measurements of the sample area and the sample volume and based on collected calibration testing information.

9. The method of claim 8, the calibrating being completed after the mounting of the hydrogen sensor on the object and including injecting a selected amount of hydrogen into the sample volume, allowing the selected amount of hydrogen to react with the hydrogen sensor for a predetermined calibration time, and measuring the amount of change in the physical property of the hydrogen sensor.

10. Diffusible hydrogen sensor apparatus for detecting initial diffusible hydrogen concentration in a solid metal object at an initial point in time, comprising:
    a sensor housing with a sealing member attached thereto disposed to surround a leak proof predetermined sample area of the object;
    the sensor housing having a predetermined sample volume within the housing adjacent the sample area to define a leak proof sample chamber;
    a hydrogen sensor with a sealed connection to the leak proof sample chamber;
    the hydrogen sensor further comprising a layer of hydrogen-reactive chemochromic material in communication with the leak proof sample chamber;
    a light source optically connected to the sensor housing to transmit light to the hydrogen sensor wherein the properties of light reflected from the layer of hydrogen-reactive chemochromic material varies as a function of hydrogen concentration in the leak proof sample chamber; and
    a detector and signal analyzer connected to the sensor housing for receiving the reflected light from the layer of hydrogen-reactive chemochromic material wherein the reflected light is detected and analyzed by the signal analyzer to correlate the variations in the light input to quantities of hydrogen in the predetermined sample volume and to then correlate an increase in such quantities of hydrogen in the sample volume to a diffusivity rate of the hydrogen diffusing from the solid metal object, and for further correlation of the diffusivity rate to the initial diffusible hydrogen concentration in the solid metal object by correlation of the diffusivity rate to a plurality of example slopes of hydrogen diffusion curves for a plurality of example initial diffusible hydrogen concentrations that are predetermined for example solid metal objects and for sampling times after the initial point in time where the rate of hydrogen evolution is compatible with the sensitivity of the hydrogen reactive chemochromic material.

11. The apparatus of claim 10 wherein the chemochromic material is selected from a group consisting of transition metal oxide, tungsten trioxide, molybdenum trioxide, yttrium dihydride, rare earth dihydride, or lanthanum dihydride.

12. The apparatus of claim 11, wherein a reflective layer of catalytic material is added to the chemochromic material that adsorbs molecular hydrogen, converts the molecular hydrogen to atomic hydrogen, and release the atomic hydrogen into the hydrogen reactive chemochromic layer.

13. The apparatus of claim 10, wherein the light source is a laser configured for emitting the transmitted light as collimated light.

14. The apparatus of claim 13, wherein the transmitted light has a wavelength of about 850 nanometers and an intensity selected from the range of about 1 to about 3 microWatts.

15. The apparatus of claim 12 wherein the reflective layer of catalytic material is selected from a group consisting of palladium or platinum.

16. The apparatus of claim 15, wherein the reflector layer has a thickness in the range of about 3 to about 30 nanometers.

17. A method of subsequent determination of an initial volume of hydrogen per unit mass of metal that was present in a particular welded metal joint specimen when the particular welded metal joint specimen was welded, comprising:

creating a set of example curves with slopes that are representative of respective diffusivity rates of hydrogen evolving from example welded metal joints as a function of time after welding for a plurality of respective example values of initial volumes of hydrogen per unit mass of metal in the example welded metal joints;

determining an actual diffusivity rate of hydrogen evolving from the particular welded metal joint in a particular time period after welding by positioning and sealing a sample chamber with a sample opening on the particular welded metal joint specimen so that hydrogen evolving from the particular welded metal joint specimen is captured in the chamber, and measuring in the time period a change of a parameter that is correlated to diffusivity rate of the hydrogen that evolves from the particular welded metal joint into the sample chamber; and determining the initial volume of hydrogen per unit mass of metal that was present in the particular welded metal joint specimen when the particular welded metal joint specimen was welded by correlating the actual diffusivity rate in the particular time period after welding with the slopes of the example curves for the same time period, wherein said time period is short enough so that the actual diffusivity rate of the hydrogen evolution is compatible with measurements of the change of the parameter.

18. The method of claim 17, wherein the parameter is intensity of light that varies as a function of hydrogen concentration in the sample chamber.

19. The method of claim 18, wherein the change of intensity of light is correlated to the diffusivity rate of the hydrogen that evolves from the particular welded metal joint specimen into the sample chamber by calibrating the intensity of light parameter to specific concentrations of hydrogen, multiplying the concentrations of hydrogen by the volume of the sample chamber to correlate the light intensity parameter to volume of hydrogen in the sample chamber, and dividing changes in the volume of hydrogen in the sample chamber by the time in which such changes in the volume of hydrogen in the sample chamber occur to correlate the measured changes of intensity of light parameter to actual diffusivity rates of hydrogen evolving from the particular welded metal joint specimen into the sample chamber.

20. The method of claim 19, including positioning a chemochromic material in the sample chamber, said chemochromic material having a characteristic light transmissivity that varies in response to exposure to hydrogen, directing a light beam to pass through the chemochromic material at least once, and measuring the parameter as loss of intensity of the beam of light upon passing through the chemochromic material.

21. The method of claim 17, wherein the parameter is a property of an electric circuit that varies as a function of hydrogen concentration in the sample chamber.

22. The method of claim 21, wherein the parameter is electric current that varies as a function of hydrogen concentration in the sample chamber.

23. The method of claim 22, including positioning a material in the sample chamber that varies in electrical resistivity in response to exposure to hydrogen, applying a voltage across the material, and measuring the electric current that flows through the material.

24. The method of claim 17, including creating the set of example curves by welding a sample welded metal joint, determining the diffusivity rate of hydrogen evolving from the sample welded metal joint by measuring the parameter in a sample time period after the sample is welded and plotting the measurements of the parameter as a function of time to obtain an actual response slope that represents the diffusivity rate, deriving an equation that closely correlates in shape and slope to the plot of the measurements of the parameter as a function of time, and developing the set of example curves from the equation for a plurality of different initial diffusion hydrogen concentrations as a function of time.

25. The method of claim 24, including deriving the equation from an error function.

26. A method of subsequent determination of an initial diffusible hydrogen concentration that was present in a particular metal specimen at a particular previous point in time, comprising:

creating a set of example curves with slopes that are representative of respective diffusivity rates of hydrogen evolving from example metal specimens as a function of time after said particular previous point in time for a plurality of respective example values of initial diffusible hydrogen concentrations in the example metal specimens;

determining an actual diffusivity rate of hydrogen evolving from the particular metal specimen in a particular time period after said particular previous point in time by positioning and sealing a sample chamber with a sample opening on the particular metal specimen so that hydrogen evolving from the particular metal specimen is captured in the chamber, and measuring in the time period a change of a parameter that is correlated to diffusivity rate of the hydrogen that evolves from the particular metal specimen into the sample chamber; and determining the initial diffusible hydrogen concentration that was present in the particular metal specimen at said particular previous point in time by correlating the actual diffusivity rate in said particular time period after said particular previous point in time with the slopes of the example curves for the same time period, wherein said time period is within a short enough time after said particular previous point in time so that the actual diffusivity rate of the hydrogen evolution is compatible with ability to provide the measurements of the change of the parameter.

27. The method of claim 26, wherein the parameter is intensity of light that varies as a function of hydrogen concentration in the sample chamber.

28. The method of claim 27, wherein the change of intensity of light is correlated to the diffusivity rate of the hydrogen that evolves from the particular metal specimen into the sample chamber by calibrating the intensity of light parameter to specific concentrations of hydrogen, multiplying the concentrations of hydrogen by the volume of the sample chamber to correlate the light intensity parameter to volume of hydrogen in the sample chamber, and dividing changes in the volume of hydrogen in the sample chamber by the time in which such changes in the volume of hydrogen in the sample chamber occur to correlate the measured changes of intensity of light parameter to actual diffusivity rates of hydrogen evolving from the particular metal specimen into the sample chamber.

29. The method of claim 28, including positioning a chemochromic material in the sample chamber, said chemochromic material having a characteristic light transmissivity that varies in response to exposure to hydrogen, directing a light beam to pass through the chemochromic material at least once, and measuring the parameter as loss of intensity of the beam of light upon passing through the chemochromic material.

30. The method of claim 26, wherein the parameter is a property of an electric circuit that varies as a function of hydrogen concentration in the sample chamber.

31. The method of claim 30, wherein the parameter is electric current that varies as a function of hydrogen concentration in the sample chamber.

32. The method of claim 31, including positioning a material in the sample chamber that varies in electrical resistivity in response to exposure to hydrogen, applying a voltage across the material, and measuring the electric current that flows through the material.

33. The method of claim 26, including creating the set of example curves by providing a sample metal specimen with an example initial diffusible hydrogen concentration at a particular previous point in time, determining the diffusivity rate of hydrogen evolving from the sample metal specimen by measuring the parameter in a sample time period after the particular previous point in time and plotting the measurements of the parameter as a function of time to obtain an actual response slope that represents the diffusivity rate, deriving an equation that closely correlates in shape and slope to the plot of the measurements of the parameter as a function of time, and developing the set of example curves from the equation for a plurality of different initial diffusion hydrogen concentrations as a function of time.

34. The method of claim 33, including deriving the equation from an error function.

35. A method of subsequent determination of an initial diffusible hydrogen concentration in a particular weld of a particular metal, comprising:

creating a set of example curve slopes that are representative of respective diffusivity rates of hydrogen evolving from a plurality of example welds of the same particular metal at a subsequent time after welding, which correlate respectively to a plurality of respective example values of initial diffusible hydrogen concentration in the example welds;

generating a curve slope that is indicative of an actual diffusivity rate of hydrogen evolving from the particular weld at a particular time after welding the particular weld that corresponds to said subsequent time by positioning and sealing a sample chamber with a sample opening on the particular weld so that hydrogen evolving from the particular weld is captured in the sample chamber, and measuring, at the particular time after welding, a change of a parameter that is correlated to diffusivity rate of the hydrogen that evolves from the particular weld into the sample chamber; and with the set of example curve slopes, correlating the curve slope that is indicative of the actual diffusivity rate of the particular weld to the example curve slopes to determine from the example curve slopes the initial diffusible hydrogen concentration that correlates to the curve slope that is indicative of the actual diffusivity rate of the particular weld.

36. The method of claim 35, wherein the parameter is intensity of light that varies as a function of hydrogen concentration in the sample chamber.

37. The method of claim 35, wherein the parameter is a property of an electric circuit that varies as a function of hydrogen concentration in the sample chamber.

38. The method of claim 35, including creating the set of example curve slopes empirically by generating a plurality of curve slopes that are indicative of diffusivity rates of hydrogen evolving respectively from a plurality of example welds at a particular time after welding, determining the initial diffusible hydrogen concentrations in respective duplicates of the example welds by standard American Welding Society protocol, and ascribing those respective initial diffusible hydrogen concentrations to the respective curve slopes.

39. The method of claim 38, including creating additional example curve slopes theoretically by formulating parameters for a diffusion equation form of an error function to conform a plurality of curve slopes obtained with the diffusion equation form of the error function to the example curve slopes that are created empirically and then calculating the additional example curve slopes using the diffusion equation and formulated parameters with varying values for the initial diffusible hydrogen concentration parameter.

40. A method of determining an actual diffusivity rate of diffusible hydrogen evolving from a sample area of a metal specimen, comprising:

positioning and sealing a sample chamber with a sample opening on the metal specimen to define the sample area and so that hydrogen evolving from the metal specimen in the sample area is captured in the sample chamber;

allowing hydrogen to evolve from the sample area of the metal specimen for a sample time period;

measuring a change of a parameter that is indicative of a change in hydrogen concentration in the sample chamber during the sample time period;

determining the change in hydrogen concentration in the sample volume by correlation with a quantitative relationship between the parameter and hydrogen concentration;

multiplying the change in hydrogen concentration by the volume of the sample chamber to determine volume of hydrogen evolved from the sample area into the sample chamber during the sample period; and dividing the volume of hydrogen evolved from the sample area by the sample time to determine the hydrogen diffusion rate from the sample area.

41. The method of claim 40, wherein the parameter is intensity of light that varies as a function of hydrogen concentration in the sample chamber.

42. The method of claim 41, including positioning a chemochromic material in the sample chamber, said chemochromic material having a characteristic light transmissivity that varies in response to exposure to hydrogen, directing a light beam to pass through the chemochromic material at least once, and measuring the parameter as loss of intensity of beam of light upon passing through the chemochromic material.

43. The method of claim 40, wherein the parameter is a property of an electric circuit that varies as a function of hydrogen concentration in the sample chamber.

44. The method of claim 43, wherein the parameter is electric current that varies as a function of hydrogen concentration.

45. The method of claim 44, including positioning a material in the sample chamber that varies in electrical resistivity in response to exposure to hydrogen, applying a voltage across the material, and measuring the electric current that flows through the material.

* * * * *